United States Patent [19]
Miller

[11] Patent Number: 5,474,523
[45] Date of Patent: Dec. 12, 1995

[54] BODY BRACE

[75] Inventor: John J. Miller, Easton, Mass.

[73] Assignee: Boston Brace International, Inc., Avon, Mass.

[21] Appl. No.: 408,131

[22] Filed: Mar. 21, 1995

Related U.S. Application Data

[63] Continuation of Ser. No. 70,711, May 28, 1993, abandoned.

[51] Int. Cl.⁶ .................................................. A61F 5/02
[52] U.S. Cl. .................................................. 602/19; 602/5
[58] Field of Search ........................... 602/5, 19; 2/44, 2/45; 128/781, 878, 882

[56] References Cited

U.S. PATENT DOCUMENTS

| | | |
|---|---|---|
| 3,871,367 | 3/1975 | Miller . |
| 5,072,725 | 12/1991 | Miller . |
| 5,074,288 | 12/1991 | Miller . |

OTHER PUBLICATIONS

Sales literature of O&P Systems, Inc. of Avon, Mass. for *The Original 15° Boston Scoliosis Brace*—reference A.
Sales literature of O&P Systems, Inc. of Avon, Mass. for *The Original 15° Boston Scoliosis Brace*—reference B.

*Primary Examiner*—Richard J. Apley
*Assistant Examiner*—Beverly M. Flanagan
*Attorney, Agent, or Firm*—Kriegsman & Kriegsman

[57] ABSTRACT

A hard body brace for treating scoliosis in a patient while preventing hypokyphosis in the patient's thoracic spine. As preferably envisioned by the present invention, the hard body brace may be fabricated by the manufacturer as an unfinished brace and may then be finished on site by an orthotist to meet the exact size and shape of the intended wearer. In a preferred embodiment, the unfinished hard body brace comprises a shell shaped to surround the torso of a person in such a way as to correct scoliosis, the shell having an outer layer of hard plastic material and an inner layer of compressible plastic material bonded to the outer layer. The shell is preferably made from a single section and has a vertically extending split portion. To prevent hypokyphosis, the shell is shaped to define a kyphotic angle in the thoracic spine of approximately 20 to 25 degrees. The shell may additionally be shaped to define a lordotic angle in the lumbar spine of approximately 15 degrees to make the brace more comfortable to the wearer.

10 Claims, 3 Drawing Sheets

BODY BRACE

This is a continuation of application Ser. No. 08/070,711, filed May 28, 1993, now abandoned.

The present invention relates generally to body braces and more particularly to a new and improved body brace.

Body braces are well-known in the art and have been used in the past for correcting various abnormalities or deformities of the spine and/or for providing support.

In U.S. Pat. No. 3,871,367 to M. E. Miller, which issued Mar. 18, 1975 and is incorporated herein by reference, there is disclosed a body brace which is constructed to be used to correct common back disorders, including scoliosis. The brace comprises an outer layer of a hard substantially rigid plastic material and an inner layer of soft compressible plastic material, with the inner layer being bonded to the outer layer. The brace is shaped to engage a person's pelvis and includes an anterior portion, a vertically split posterior portion, releasable fastening means secured to the adjacent posterior portions to aid in securing the brace to a wearer, and inwardly curved sections in both layers of the brace for engaging the iliac crests of the wearer, the inwardly curved sections having appreciably thicker compressible inner layers therein. The brace has been marketed by O&P Systems, Inc. of 20 Ledin Drive, Avon, Mass., under the trademark Boston Body Brace.

Another known type of body brace constructed to be used for corrective purposes comprises a shell which is sized and configured so as to circumscribe the trunk of the body and having a vertical length so as to extend at the posterior side from approximately the sacrum to approximately the eighth dorsal and at the anterior side from approximately the pubic region to approximately the upper limit of the diaphragm, the shell being comprised of a flexible sheet of hard substantially rigid plastic material structured to provide a girdle having a continuous posterior side, overlapping anterior sides and lateral sides, the lateral sides containing indentations commencing at the posterior side extending forwardly therefrom and terminating at the anterior side and embodying laterally divergent portions above and below the indentations dimensioned to receive, respectively, the lower part of the rib cage and the upper part of the pelvis, transversely-spaced, vertically disposed parallel stays fixed to the girdle at substantially equal distances from the ends of the overlapping anterior sides and cinches connected to the respective stays adjustable to constrain the girdle about the body. This body brace is also marketed by O&P Systems, Inc. of 20 Ledin Drive, Avon, Mass., under the trademark Boston Overlap Brace.

Both of the above-described braces are known in the art as hard body braces because they contain at least one layer of a hard substantially rigid material.

One of the problems frequently associated with hard body braces designed to correct scoliosis is that they are typically flat, i.e., lack curvature, in the thoracic spine. Consequently, after being worn for extended periods of time, such body braces tend to flatten the thoracic spine of the wearer to conform to their own rigid shape. This flattening of thoracic spine, which is also known as hypokyphosis, is undesirable since some curvature of the thoracic spine is normal. (The Spinal Research Society, an organization of orthopedic surgeons, has determined that approximately 20 to 40 degrees of curvature, measured using the Cobb method, is normal. A normal degree of curvature in the thoracic spine is referred to as kyphosis.)

Recently, in an effort to prevent hypokyphosis of the thoracic spine while treating scoliosis, hard body braces have been experimented with which are shaped to define (1) a 15 degree angle in the thoracic spine or (2) a 30 degree angle in the thoracic spine. It appears, however, that the 15 degree brace does not sufficiently prevent hypokyphosis (since less than about a 20 degree angle in the thoracic spine is not considered normal) and that the 30 degree brace is too painful for most patients to wear due to the magnitude of the angle in the thoracic spine.

Other patents of interest to the present invention include U.S. Pat. No. 5,074,288 to M. E. Miller, which issued Dec. 24, 1991, and U.S. Pat. No. 5,072,725 to M. E. Miller, which issued Dec. 17, 1991. Both of these patents, which are also incorporated herein by reference, relate to soft body braces.

SUMMARY OF THE INVENTION

It is an object of the present invention to provide a new and improved body brace.

It is another object of the present invention to provide a body brace as described above which is designed to control kyphosis of the thoracic spine while treating scoliosis.

It is still another object of the present invention to provide a body brace which is easy to manufacture and is effective when worn.

It is still yet another object of the present invention to provide an unfinished body brace which can easily be finished to provide a body brace customized to the size and shape of the intended wearer.

It is still yet a further object of the present invention to provide an unfinished body brace as described above which can be customized on site to make a finished body brace.

In accordance with the purpose of the invention as broadly set forth above and as will hereinafter be described in greater detail, a body brace constructed according to the teachings of the present invention is provided which comprises a shell, the shell comprising one or more sections sized and shaped to surround the torso of a person and defining a kyphotic angle of approximately 20 to 25 degrees in the thoracic spine as defined by the Cobb method.

In a preferred embodiment, the body brace is additionally designed to correct scoliosis, the shell being made from a single section sized and shaped to surround the torso of a person and comprising an outer layer of a hard substantially rigid plastic material and an inner layer of a soft compressible plastic material bonded to the outer layer. The inner and outer layers of the shell define a vertical split in the posterior portion of the shell. The shell is further shaped to define a lordotic angle of approximately 15 degrees in the lumbar spine.

The body brace of the present invention may be either finished or unfinished, the unfinished body brace being fabricated by the manufacturer and then finished on site by the orthotist to meet the size and shape of the intended wearer. The finished body brace preferably further comprises one or more fasteners secured to the split portion of the shell.

Various objects, features and advantages will appear from the description to follow. In the description, reference is made to the accompanying drawings which form a part thereof, and in which is shown by way of illustration, specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF PREFERRED EMBODIMENTS

Figure 2:
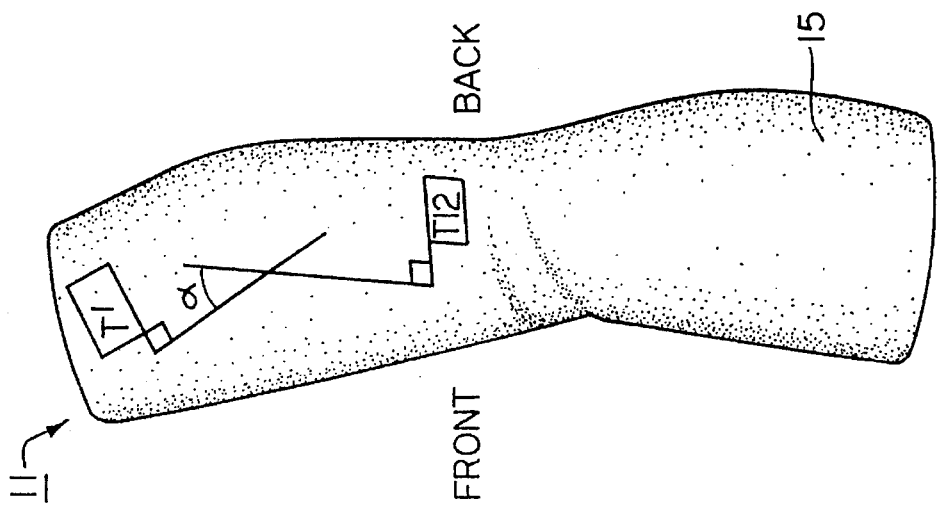
FIG. 2 is a right side view of the unfinished body brace of FIG. 1, the kyphotic angle α of approximately 20 to 25 degrees in the thoracic spine of the brace being illustrated.
Figure 1:
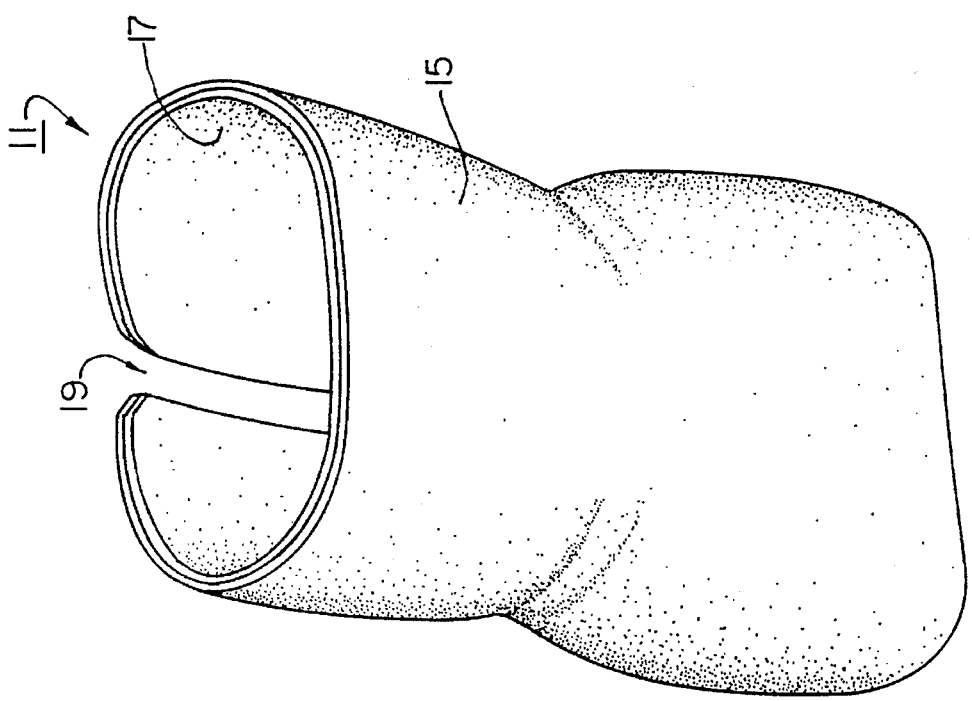
FIG. 1 is a front, top perspective view of one embodiment of an unfinished body brace constructed according to the teachings of the present invention.

The present invention is directed to a hard body brace designed to correct scoliosis in a patient while, at the same time, correcting and/or preventing hypokyphosis of the patient's thoracic spine. Hypokyphosis commonly afflicts sufferers of scoliosis and/or is often caused or aggravated by scoliosis braces of the type employed in the past. Hypokyphosis of the thoracic spine is said to occur when the angle defined by the perpendiculars to the first and twelfth thoracic vertebrae is less than about 20 degrees and is not lordotic. (The aforementioned method of determining the angle between two vertebrae is commonly referred to as the Cobb method.)

Referring now to FIGS. 1 through 5, there are shown various views of an unfinished hard body brace constructed according to the teachings of the present invention, the unfinished hard body brace being represented generally by reference numeral 11.

Unfinished brace 11 consists of a shell, the shell being generally sized and shaped to surround the torso of a person and itself consisting of an outer layer 15 of a hard, substantially rigid plastic material and an inner layer 17 of a soft, compressible plastic material which is bonded to outer layer 15 over the entire surface thereof. The respective thicknesses of outer layer 15 and inner layer 17 and examples of materials suitable for use in outer layer 15 and inner layer 17 are well-known to those of ordinary skill in the art and do not form a part of the present invention.

Figure 4:
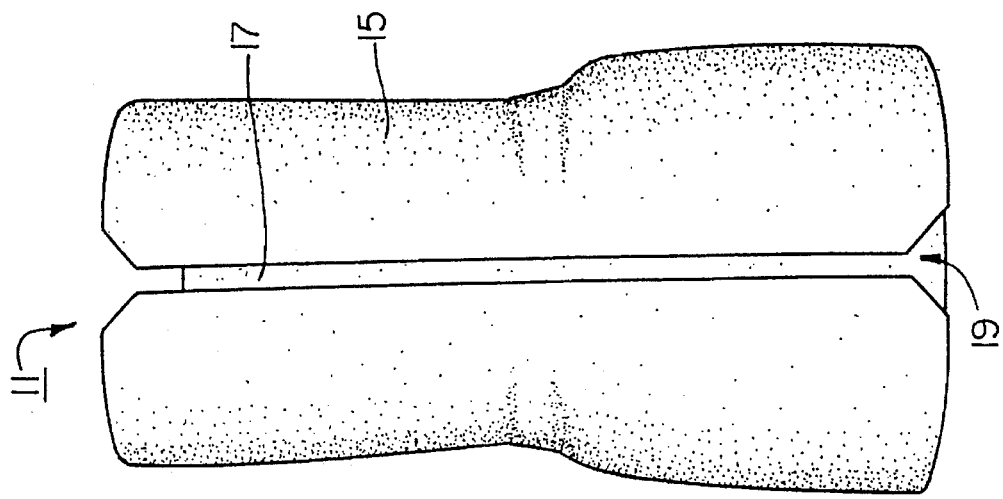
FIG. 4 is a rear view of the unfinished body brace shown in FIG. 1.
Figure 3:
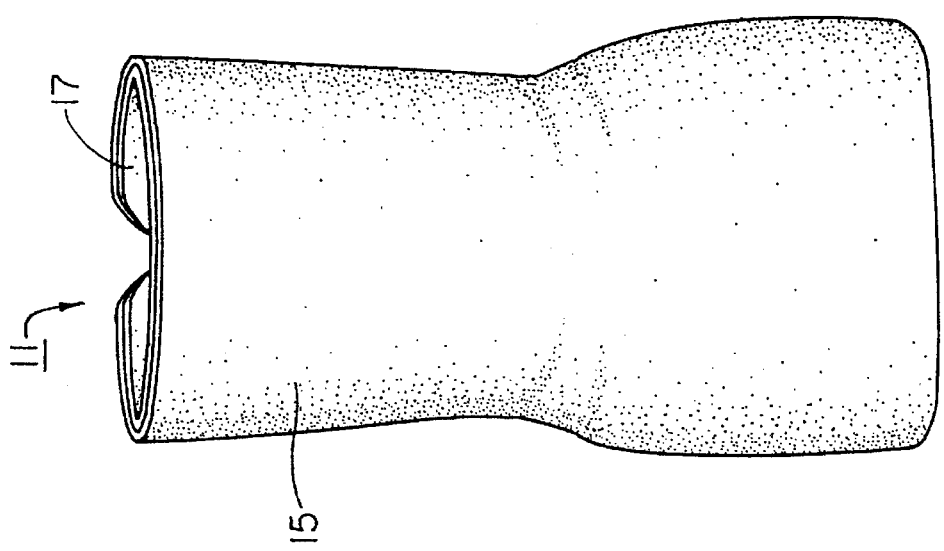
FIG. 3 is a front view of the unfinished body brace shown in FIG. 1.

As can be seen best in FIG. 4, outer layer 15 and inner layer 17 jointly define a split 19 in the posterior portion of the shell, split 19 facilitating the mounting and removal of brace 11 on a wearer.

As seen best in FIG. 2, brace 11 is shaped in the thoracic region to define a kyphotic angle α of approximately 20 to 25 degrees and of preferably 20 degrees. (Angle α is shown defined in FIG. 2 by the Cobb method between the first $T^1$ and twelfth $T^{12}$ thoracic vertebrae.) As has been mentioned above, the prinicpal reason for incorporating angle α into brace 11 is to treat and/or to prevent hypokyphosis in the wearer of the brace.

In addition to being shaped to include kyphotic angle α in the thoracic spine, brace 11 is also preferably shaped to include a lordotic angle of approximately 15 degrees in the lumbar spine for the principal reason of providing increased comfort to the wearer.

Figure 6:
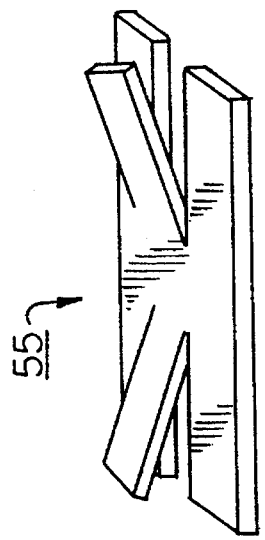
FIG. 6 is an enlarged perspective view of the fastener shown in FIG. 5 used to secure the vertically split portion of the finished body brace shell.
Figure 5:
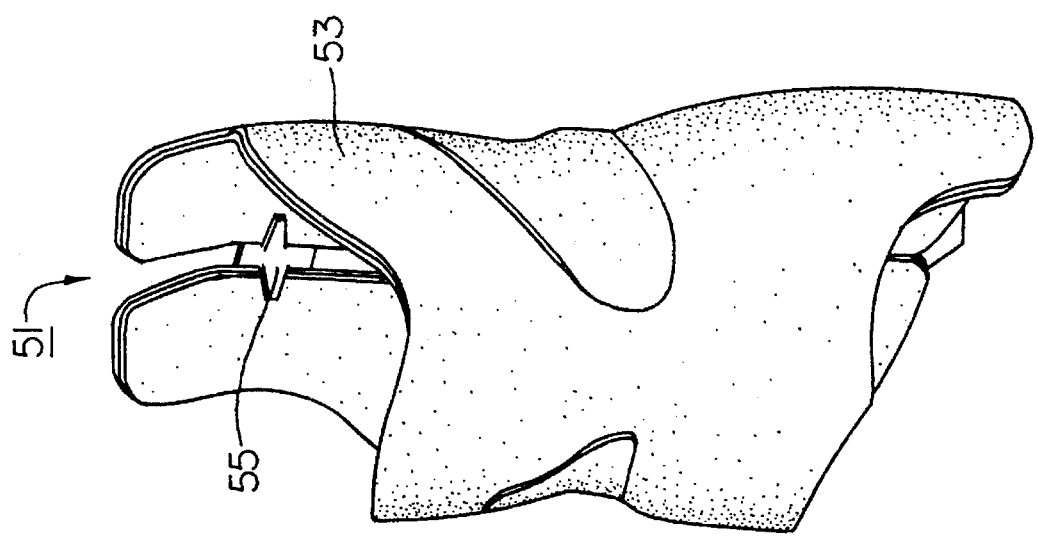
FIG. 5 is a front perspective view of a finished body brace fabricated from the unfinished body brace shown in FIG. 1.

As described above, unfinished body brace 11 has not been customized to meet the specific shape and size requirements of the intended wearer, and the fasteners needed to keep the brace from opening at the split portion have not been attached to the shell. The specific manner in which brace 11 may be finished, i.e., customized for an intended wearer, is considered to be well known to those of ordinary skill in the art and does not form a part of the present invention. Referring to FIG. 5, there is shown a front perspective view of a finished body brace 51 which has been fabricated from unfinished body brace 11, brace 51 comprising a shell 53 and one or :more fasteners 55. FIG. 6 shows in greater detail one of the fasteners 55 used to keep body brace 51 from opening at the vertically split portion of shell 53.

The embodiments of the present invention are intended to be merely exemplary and those skilled in the art shall be able to make numerous variations and modifications to it without departing from the spirit of the present invention. The above and other such variations and modifications are intended to be merely within the scope of the present invention as defined in the appended claims.

What is claimed is:

1. A body brace comprising a shell, said shell comprising one or more sections sized and shaped to surround the torso of a person and defining a kyphotic angle of approximately 20 to 25 degrees as measured between the respective perpendiculars to the first and twelfth thoracic vertebrae.

2. The body brace as claimed in claim 1 wherein said shell comprises an outer layer of a hard substantially rigid plastic material and an inner layer of a soft compressible plastic material bonded to said outer layer.

3. The body brace as claimed in claim 2 wherein said shell is made from a single section, said inner and outer layers of said shell defining a vertical split in the posterior portion of said shell.

4. The body brace as claimed in claim 1 wherein said shell is further shaped to define a lordotic angle of approximately 15 degrees in the lumbar spine.

5. A finished body brace for engaging the torso of a person for orthopedic purposes, said finished body brace comprising:

a) a shell made up of one or more sections, said shell being sized and shaped to surround the torso of a person on whom the brace is to be worn and defining (i) a kyphotic angle of approximately 20 to 25 degrees as measured between the respective perpendiculars to the first and twelfth thoracic vertebrae and (ii) a split portion; and b) one or more fasteners secured to said split portion of said shell.

6. The finished body brace as claimed in claim 5 wherein said split portion extends vertically in the posterior of said shell.

7. The finished body brace as claimed in claim 5 wherein said shell is made from a single section having an outer layer of a hard substantially rigid plastic material and an inner layer of a soft compressible plastic material bonded to said outer layer.

8. The finished body brace as claimed in claim 5 wherein said shell is also shaped to define a lordotic angle of approximately 15 degrees in the lumbar spine.

9. The body brace as claimed in claim 1 wherein said kyphotic angle is 20 degrees.

10. The finished body brace as claimed in claim 5 wherein said kyphotic angle is 20 degrees.

* * * * *